(12) United States Patent
Stoop et al.

(10) Patent No.: US 6,370,431 B1
(45) Date of Patent: Apr. 9, 2002

(54) PACEMAKER SYSTEM FOR PREVENTING VENTRICULAR TACHYCARDIA

(75) Inventors: Gustaaf A. P. Stoop, Dieren; Geeske Van Oort, Nieuwleusen; Christianus J. J. E. Van Groeningen, Utrecht; Bernhard A. P. De Vries, Dieren, all of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/237,815

(22) Filed: Jan. 27, 1999

Related U.S. Application Data

(63) Continuation-in-part of application No. 09/179,043, filed on Oct. 26, 1998.

(51) Int. Cl.[7] .......................... A61N 1/365; A61N 1/362
(52) U.S. Cl. ............................................ 607/14; 607/25
(58) Field of Search ...................... 607/14, 25; 600/516

(56) References Cited

U.S. PATENT DOCUMENTS

| | | | |
|---|---|---|---|
| 5,247,930 A | 9/1993 | Begemann et al. | 607/11 |
| 5,271,393 A | 12/1993 | Callaghan | 607/14 |
| 5,306,293 A | * 4/1994 | Zacouto | 607/17 |
| 5,782,887 A | * 7/1998 | van Kricken et al. | 607/25 |
| 5,861,011 A | * 1/1999 | Stoop | 607/25 |
| 5,978,711 A | * 11/1999 | Van Hove | |
| 5,991,659 A | * 11/1999 | de Vries et al. | 607/9 |
| 6,058,328 A | * 5/2000 | Levine et al. | |
| 6,161,041 A | * 12/2000 | Stoop et al. | 607/14 |

OTHER PUBLICATIONS

Puddu, Paolo E. et al., "The QT-Sensitive Cybernetic Pacemaker: A New Role for an Old Parameter," PACE, vol. 9, Jan.-Feb. 1986, Part I, pp. 108–123.

Internet Printout: http://www.ncbi.nlm.nih.gov/htbin, PubMedQuery, "Iatrogenic torsade de Poointes induced by thioridazine," by P. Paoloni et al., [article in Italian] May 28, 1998.

G.H Fontaine et al., "Electrophysiology of Torsades De Pointes", World Symposium on Cardiac Pacing, 6th, Montreal, PACESYMP, 1979, p. 6.3, Oct. 20, 1998.

* cited by examiner

Primary Examiner—Carl H. Layno
(74) Attorney, Agent, or Firm—Thomas F. Woods; Michael J. Jaro; Harold Patton

(57) ABSTRACT

There is provided a pacemaker system which includes intervention for overdriving the patient's natural heart rate in the event of a sensed incipient ventricular arrhythmia condition, and particularly torsades de pointes. The pacemaker continually acquires QT signals and analyzes them for respective properties, updating statistical information relating to the properties. In a preferred embodiment, the pacemaker analyzes QT interval, QT dispersion, time derivative of the QT interval, and/or T-wave amplitude and determines an intervention for pacing therapy based upon changes to these properties. The pacemaker also monitors premature ventricular beats and generates data representative of such occurrences, which data is used alone or in combination with QT data in determining whether intervention is indicated, for adjusting the intervention pacing rate. There is thus provided a systematic approach for monitoring relevant data so as to reliably determine when intervention pacing therapy is needed, and for adjusting the intervention pacing rate.

11 Claims, 10 Drawing Sheets

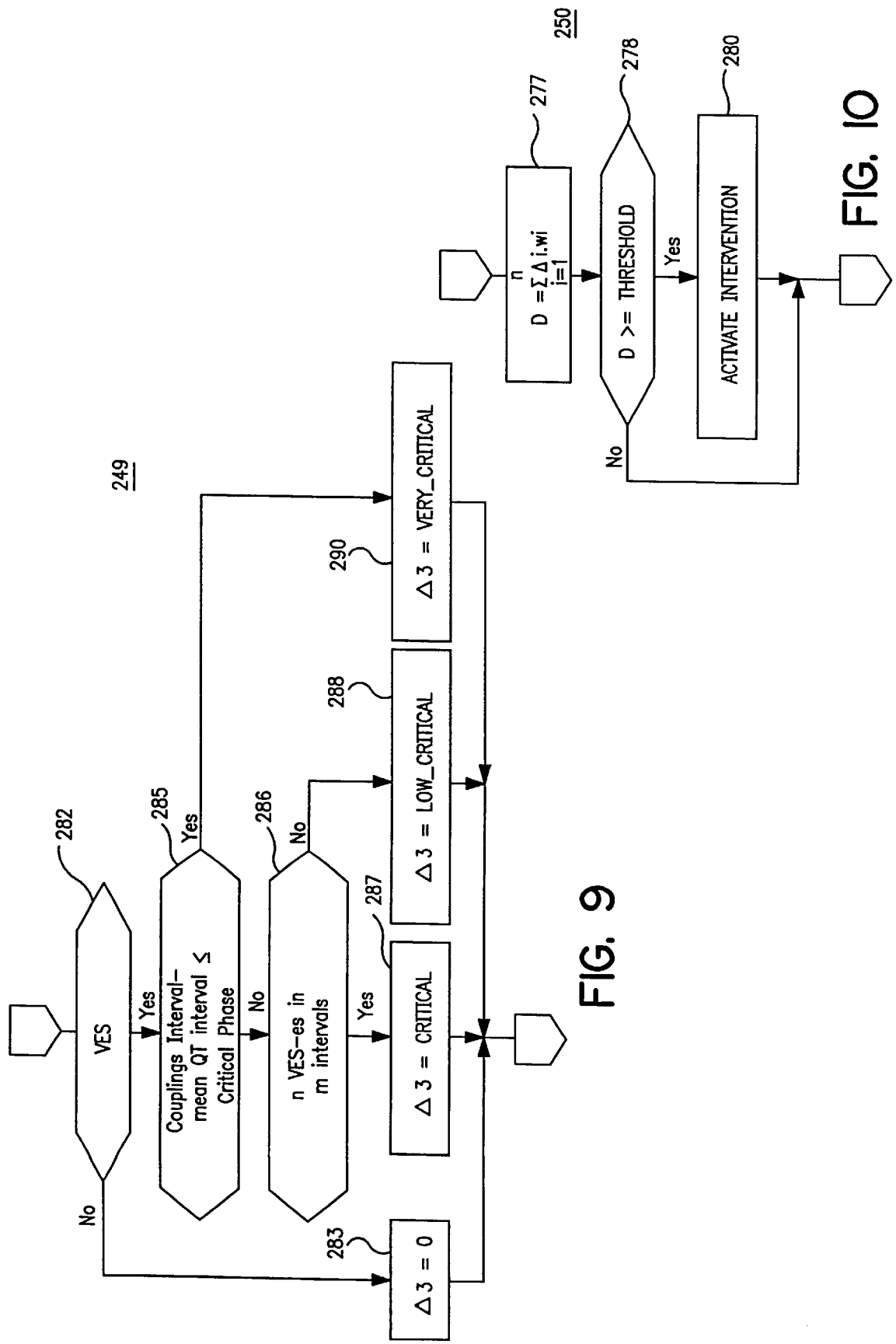

PACEMAKER SYSTEM FOR PREVENTING VENTRICULAR TACHYCARDIA

CROSS-REFERENCE TO RELATED APPLICATION

This application is a continuation-in-part of U.S. application Ser. No. 09/179,043, filed Oct. 26, 1998, and assigned to the same assignee.

FIELD OF THE INVENTION

This invention relates to cardiac pacing systems and, more particularly, pacing systems having a capability of detecting and treating long QT syndrome.

BACKGROUND OF THE INVENTION

It is known that prolongation of the QT interval frequently results in serious ventricular arrhythmias, and might be a predictor of torsades de pointes (TdP) and sudden death. See, "Electrophysiology of Torsades de Pointes," Fontaine et al., World Symposium on Cardiac Pacing, $6^{th}$, Montreal, PACESYMP, 1979, p. 6.3. As set forth in the Fontain et al. article, TdP is manifested by an ECG pattern which occurs as a transient life-threatening ventricular arrhythmia, frequently announced by bradycardia, long QT intervals, very large T waves and premature ventricular contractions (PVCs). The term Ventricular Extra Systole (VES) is used herein synonymously with PVC. The premature ventricular beats that occur at the onset of long QT syndrome appear around the end of the large T waves, and the number of such VESs increases with time, leading to couplets or triplets and eventually to a degeneration of the rapid arrhythmia which characterizes TdP. A VES originates in the ventricle, and is considered a PVC when it comes "early" with respect to the previous VS.

QT prolongation as a predictor of the onset of ventricular arrhythmia is known in the literature. See "QT-Sensitive Cybernetic Pacemaker: A New Role For An Old Parameter?", Puddu and Torresani, *PACE,* Vol. 9, January–February 1986, Part 1, pp. 108–123. Overdrive pacing is suggested as an effective therapeutic tool in both congenital and acquired QT prolongation. See also U.S. Pat. No. 5,217,393, disclosing a pacemaker wherein during each cardiac cycle the QT wave form is monitored and integrated and a ventricular gradient is obtained. Overdrive pacing is triggered when the gradient increases above a predetermined threshold. Although the literature identifies certain features of the cardiac signal which may be predictors of the onset of the ventricular arrhythmia such as TdP and ventricular fibrillation, often leading to syncope and sudden death, what is needed in the art is a pacemaker which systematically acquires data and processes it so as to be able to determine, with a high degree of statistical probability exactly when there is an onset of ventricular arrhythmia. For example, QT prolongation by itself is likely, for most patients, to be an insufficient predictor of a true onset of TdP or another ventricular arrhythmia. Rather, what is required is processing of sensed cardiac signal data, the processing being done systematically so as to make a continuous determination of the probability of the onset of such a ventricular arrhythmia, thereby enabling effective pacing treatment of the patient condition.

More broadly, there is a need in the art for providing a more systematic and reliable means of determining when patient conditions suggest the onset of a dangerous ventricular arrhythmia, and for providing an effective overdrive pacing therapy to prevent such arrhythmia. For instance, it is known that patients can be vulnerable to ventricular tachycardia (VT) during the awakening hours, while TdP emerging from Long QT syndrome and other ventricular arrhythmias can occur at any time. Thus, there is a need for a more reliable pacemaker technique for detecting the onset of a ventricular arrhythmia whenever it might occur, and for providing appropriate pacing therapy.

SUMMARY OF THE INVENTION

It is an object of this invention to provide a pacemaker system having the capability of detecting conditions indicative of Long QT Syndrome, and for providing appropriate pacing therapy in response to these indications. In particular, the pacing therapy is designed to respond so as to reduce disparity of ventricular refractoriness and prevent torsades de pointes, and consequent sudden death.

It is a further object of this invention to detect the onset of a dangerous ventricular arrhythmia, and to provide intervention to prevent such an arrhythmia, either during patient awakening or otherwise.

In accordance with the above object, there is provided a pacemaker system and method of pacing, having an improved arrangement for analyzing patient QT information on an ongoing basis, and for determining the occurrence of statistically significant changes in a plurality of QT parameters, thereby providing an accurate determination of when TdP or other VT is indicated. The different QT parameters are preferably analyzed cyclically, and statistical data representative of each of said parameters is recalculated following each sensed QT signal. In a preferred embodiment, QT data is compiled in a histogram form, in accordance with different rate bins, or intervals. The current QT interval is compared with the compiled mean value of QT interval for the appropriate rate bin, and it is determined whether the QT interval has increased by more than twice the standard deviation of the mean. In a preferred embodiment, similar calculations are made for measures of QT dispersion and the time derivative of QT changes in T-wave amplitude and morphology can be measured and processed in a like manner. Additionally, the pacemaker determines whether a VES has occurred, and if so, what has been the recent rate of occurrence of VESs. This data is used to calculate whether pacing at an intervention rate above the patient's natural rate is indicated, and if so how to adjust the intervention rate. By this means, the pacemaker system provides overdrive pacing which is accurately responsive to cardiac conditions representative of ventricular tachycardia, like TdP, or another dangerous ventricular arrhythmia.

BRIEF DESCRIPTION OF THE DRAWINGS

FIG. 9 is a simplified flow diagram illustrating the primary steps taken in carrying out the Ventricular Extra Systole analysis portion of the VT Prevention Routine of FIG. 7.

FIG. 10 is a simplified flow diagram illustrating the primary steps taken in carrying out the Determine Intervention portion of the VT Prevention routine of FIG. 7.

DESCRIPTION OF THE PREFERRED EMBODIMENTS

In the discussion hereinbelow of the preferred embodiments, the following abbreviations and symbols are used:

| Symbol | Description |
| --- | --- |
| IRn | step in Intervention_Rate belonging to a certain property (min$^{-1}$) |
| Intervention_) | total step in Intervention_Rate (= E IRn) [min$^{-1}$] |
| LRL | Lower Rate Limit |
| UPL | Upper Pacing Limit |
| SD | Standard Deviation |
| TdP | Torsades de Pointes |
| DPL | Dynamic Pacing Limit |
| VES | Ventricular Extra Systole, or Premature Ventricular Contraction |
| VT | Ventricular Tachycardia |

Also, as used herein, the term QT or QT signal, embraces both the QRS (depolarization) portion and T wave (repolarization) portion of the ventricular signal, either spontaneous or evoked by pacing. Thus, the term QT signal also includes the interval between the QRS and T wave portions, as well as other parameters including slope, integral of the signal, time derivative, etc. The term "recent" is used in reference to stored data representative of collected QT properties, e.g., as in histogram form illustrated by the preferred embodiment. The term "Long QT Syndrome" is used in the same manner as the literature on the subject, and refers to conditions which generate into rapid arrhythmias such as TdP and other ventricular arrhythmias.

Figure 1:
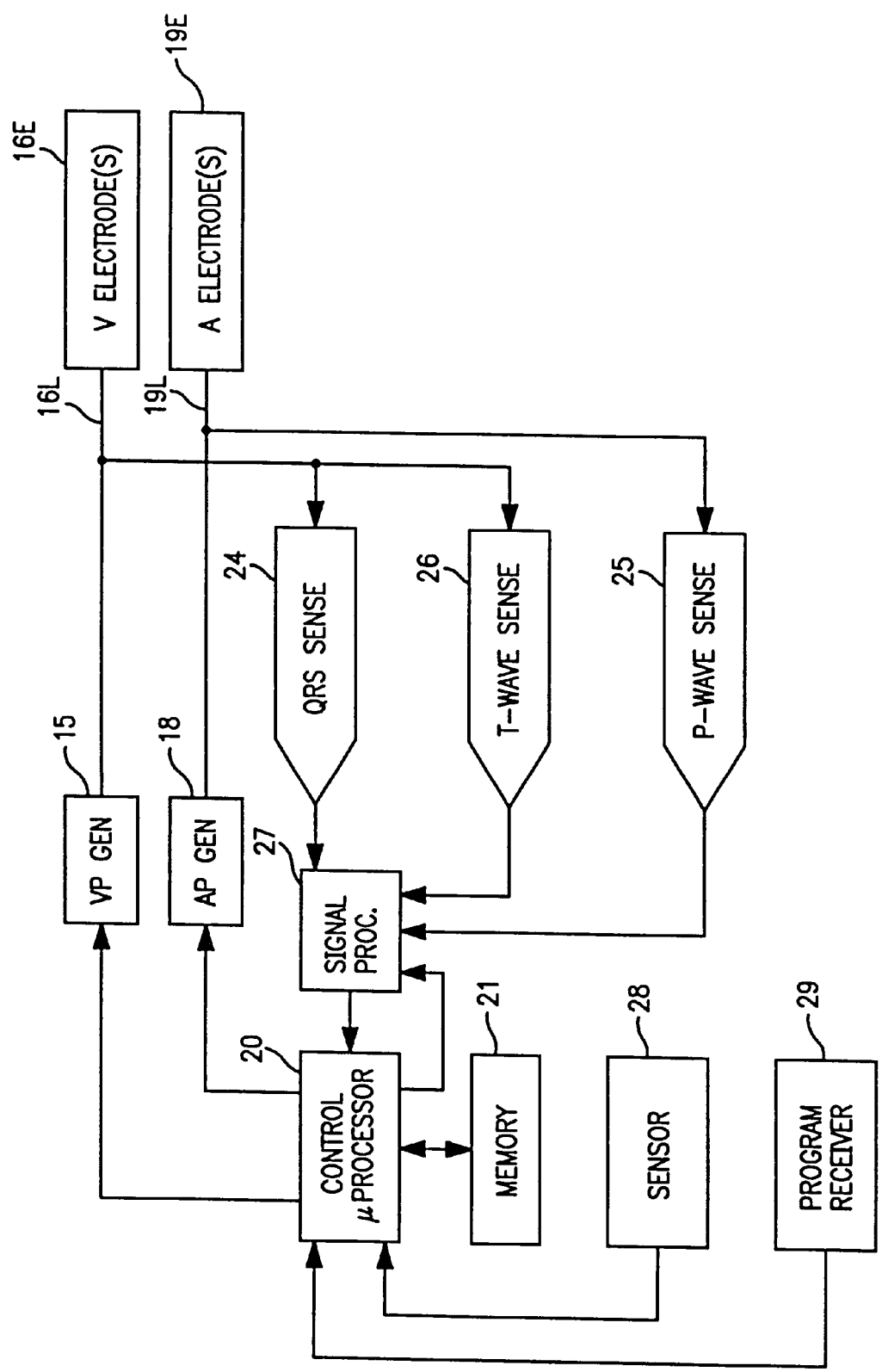
FIG. 1 is a block diagram of the primary hardware and functional components of a pacemaker system in accordance with this invention.

Referring now to FIG. 1, there is shown a block diagram illustrating the primary components of a pacemaker system in accordance with this invention. A ventricular pulse generator 15 is controlled under control block 20 to generate ventricular pacing pulses, which are delivered to the patient's heart through lead 16L through to ventricular electrodes 16E. Likewise, for a dual chamber pacemaker, atrial pulse generator 18 also is controlled by block 20, and generates atrial pace pulses which are delivered through lead 19L to atrial electrodes 19E. The signals sensed at the ventricular electrodes are amplified at QRS circuitry 24 and T wave sense circuitry 26, respecctively, the outputs of which are connected to signal processing block 27, and then transferred to control block 20. Likewise, signals sensed in the atrium by atrial electrode or electrodes 19E are amplified at P wave sense circuitry 25 processed at block 27, and connected back to control block 20. As discussed further below, block 27 preferably is dedicated DSP hardware. Control block 20, in the preferred embodiment, contains a microprocessor, and is in two-way connection with suitable memory 21. As discussed hereinbelow, the logic steps taken in the practice of this invention are preferably handled by software. Also shown in FIG. 1 is a sensor or sensors 28, which can be used for rate control in a known manner; the QT interval obtained from the signals outputted by sense circuits 24 and 26 can also be used for rate control. A program receiver (and transmitter) 29 is used to receive program instructions from an external programmer, which are downloaded through control block 20. In the context of this invention, the analysis of QT data, discussed in detail hereinbelow, can be changed by downloading one or more replacement routines. This may be desirable, e.g., in a case where experience has shown that for the patient involved, one or another of the QT parameters should be weighted differently.

Figure 2:
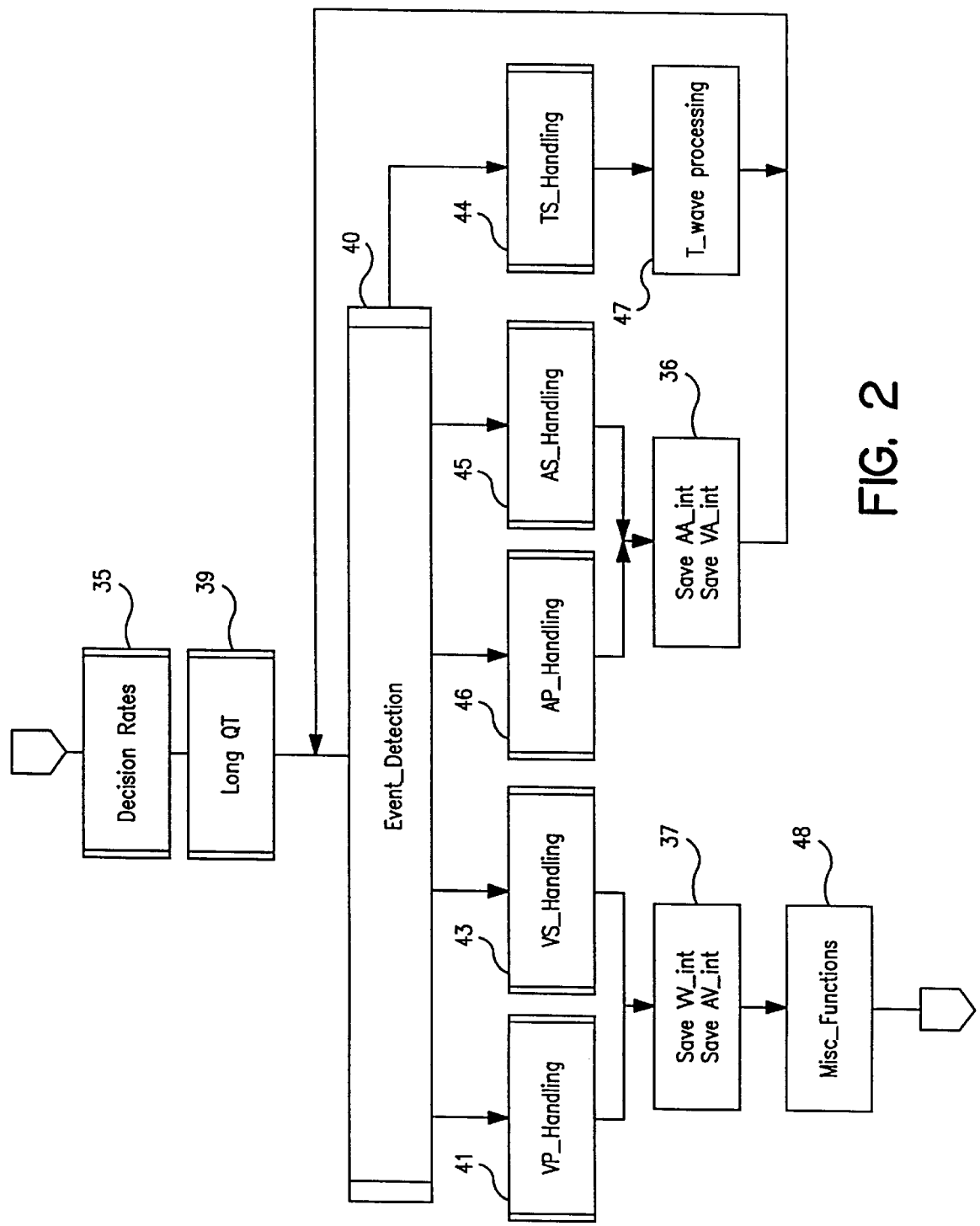
FIG. 2 is a flow diagram illustrating the primary cyclical functions of a pacemaker in accordance with this invention, whereby the pacemaker detects various events, and handles (responds to) those events, in combination with a Long QT routine for determining when overdrive pacing therapy is indicated.

Referring now to FIG. 2, there is shown a flow diagram which illustrates the "Long QT" routine together with other functions carried out cyclically in sensing and a pacing. In a preferred embodiment, decision rates are determined cyclically, as shown at 35. These include phys_rate (which is a measure of the patient's natural rate), and the dynamic pacing limit (DPL), which is coupled to phys_rate and sets the normal escape interval for pacing. See U.S. Pat. No. 5,247,930, incorporated herein by reference. Long QT routine 39 is represented by blocks 50–53 set forth in FIG. 3, and is the overall routine for analyzing QT and VES data and determining whether intervention pacing is called for, and if so, how to adjust the intervention rate. As is observed in the discussion below of the details of the routine for determining intervention therapy, the routine may call for intervention therapy based on determination of a long QT interval as such, but may also call for such therapy where the QT interval is not necessarily deemed "long", but other changes in the QT signal are observed.

The remainder of FIG. 2 represents cyclical event detection and response, i.e., handling by the pacemaker in response to a given event. In the event of an atrial sense (AS) at block 40, the pacemaker goes to the AS-handling routine 45, where the sense signal is analyzed for determination of the next step, whether the atrial signal can be tracked. The values of AA_int (which represents current rate) and VA_int are saved at 36. Following this, the routine goes back to event detection block 40 and awaits a ventricular event. If the atrial escape interval has timed out, the pacemaker goes to routine 46 (AP_handling) where an atrial pace pulse is delivered.

If a ventricular sense has been detected, the pacemaker goes to block 43 and handles the VS. Likewise, if the ventricular escape interval (V_esc) has timed out, the pacemaker goes to block 41 and delivers a ventricular pace pulse (VP). Following either ventricular event, at 37 values of VV_int and AV_int are saved.

When a T-wave is sensed, the pacemaker does TS_handling at 44, and T_wave processing at 47. The processing is suitably done by DSP, and results in storage of QT signal data from which the analysis carried out in the Long QT routine is done. This data includes QT_int data and T-wave data.

Figure 3:
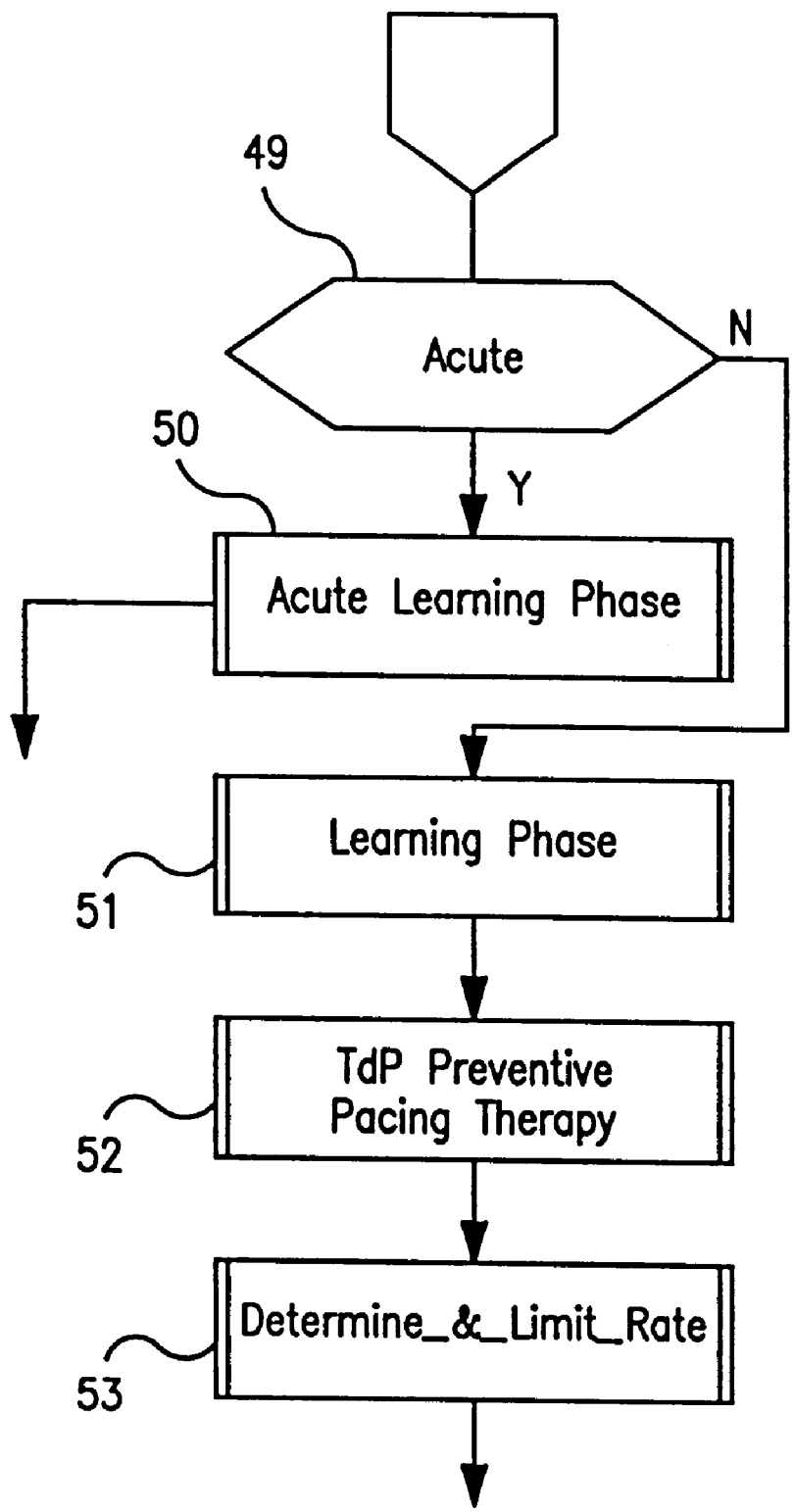
FIG. 3 is a block diagram showing the different routines carried out by the pacemaker for determining the characteristics of Long QT Syndrome and for providing response therapy.

Referring now to FIG. 3, there is shown a flow diagram which represents the four main routines of the Long QT routine 39. At time of implant, the pacemaker is in an acute state, as seen at 49. Consequently, the Acute Learning Phase is entered at 50. During the Acute Learning Phase 50, the pacemaker accumulates data concerning the QT signal, which is used to build up profiles for subsequent use in monitoring for a malignant arrhythmia. There is insufficient time for a long learning period, and consequently the "Acute Learning Phase" is carried out only for acute measuring of the normal or standard properties of the QT signal parameters that are used, which is done preferably in-hospital tests. When the pacemaker is ready to proceed from the Acute Phase, it may be programmed to go directly to the Learning Phase 51 each cycle.

Referring to block 51, this routine is run cyclically to update QT data. Thus, the properties of the preselected parameters of the QT signal which are used for detecting TdP, are continuously adapted, so that changes can be detected. Following this, at routine 52, the pacemaker determines whether TdP preventive pacing therapy is indicated, and if so, how to adjust the intervention pacing rate. At routine 53, the determined intervention rate is checked to make sure that it is within appropriate limits. After this, the pacemaker leaves the Long QT overall routine and goes to perform the sense-pace functions as discussed above in FIG. 2.

Figure 4A:
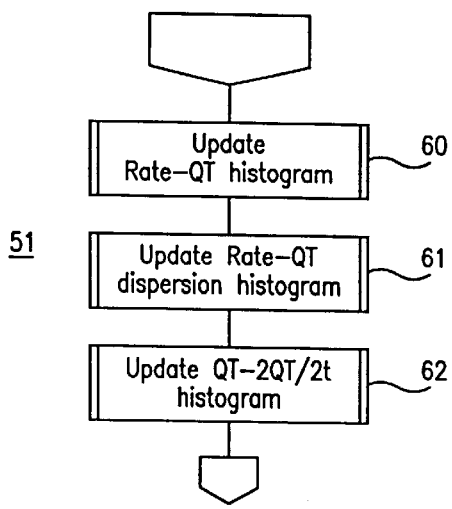
FIG. 4A is a brief flow diagram indicating the steps taken during the learning phase of the Long QT Syndrome routine.
Figures 4B, 4C, 4D:
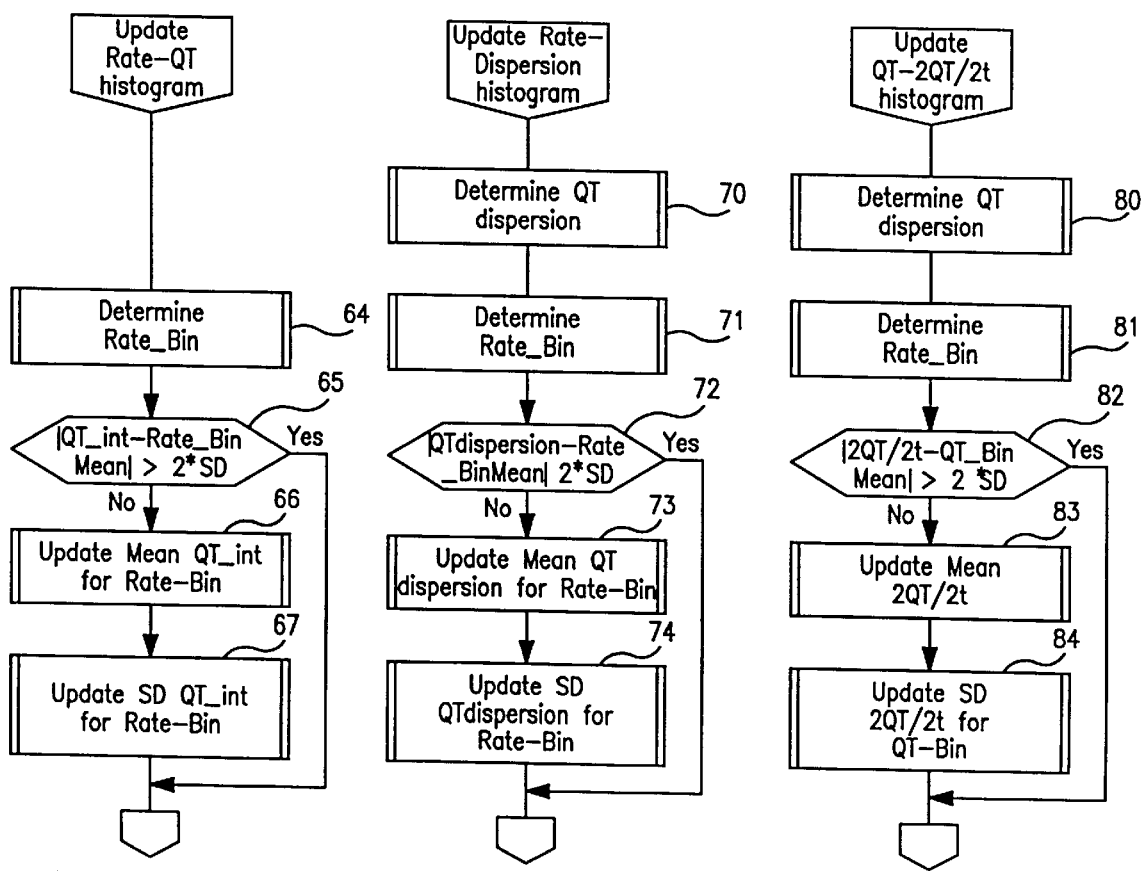
FIG. 4B is a flow diagram illustrating the primary steps taken in obtaining QT data.
FIG. 4C is a flow diagram illustrating the primary steps taken in obtaining and updating QT dispersion data.
FIG. 4D is a flow diagram illustrating the primary steps taken in obtaining and updating QT dynamics data.

Referring now to FIGS. 4A, 4B, 4C and 4D, there are shown flow diagrams representing details of the Learning Phase routine 51. FIG. 4A is a top level flow diagram of routine 51. At 60 the recently acquired QT data is utilized to update a rate-QT histogram. As seen in FIG. 4B, the first step is to determine the appropriate Rate_Bin. Thus, in accumulating histogram data, the data is compiled in respective bins representing respective rate ranges. When updating the Rate-QT histogram, the first step undertaken at 64 is to determine the appropriate rate bin, corresponding to the rate as was stored at block 48. Then, at 65, the routine examines the current value of QT_int, compared to the mean value for the Rate_Bin that is being examined. If the absolute value of this difference is greater than two times the standard deviation (SD), the measures are not used to update the bins, and the routine exits. If this difference is less than or equal to 2*SD, the routine goes to 66, where the pacemaker calculates and updates the value of the mean QT_int for the Rate_Bin which is involved. Then, at 67, the SD QT_int is calculated and updated for the Rate_Bin.

Referring back to routine 61 of FIG. 4A, the pacemaker updates the Rate-QT dispersion histogram. This involves updating histogram data which compiles values of QT dispersion for different rate bins. QT dispersion, or QTd, is measured to reflect the difference between local maxima and minima values of the QT interval, and is associated with increased risk of ventricular tachycardia and sudden cardiac death. QT dispersion is a reflection of refractory dispersion. QT dispersion is suitably obtained by obtaining templates of the QRS (depolarization) and T wave (repolarization) portions of the QRS signal. In obtaining such templates, the wave signal data is suitably placed in the digital form in block 27; obtaining wave form templates is well known in the art and any suitable hardware or software arrangement can be used in this invention. Differences of the respective wave form amplitudes along successive time increments are determined by subtraction of the wave form amplitude values, and the differences are integrated over the time domain. In a preferred embodiment, the template generation and template difference calculations are performed by dedicated hardware. See the further discussion below of template generation in connection with FIG. 7. However, any combination of hardware and software can be utilized. After determination of QT dispersion, at 71 the appropriate rate bin is determined, and then at 72 the absolute difference of the current value of QT dispersion and the mean value for the selected Rate_Bin is compared to 2*SD. If this value is greater than 2*SD, the routine exits. If the difference value is less than or equal to 2*SD, the routine goes to 73 and updates the mean QT dispersion for the current Rate_Bin; and at 74 the SD QT dispersion is updated for the rate bin.

Returning to block 62 of FIG. 4A, the pacemaker updates the 2QT/2t histogram. The specific steps of this histogram updating are set forth in FIG. 4D. The current value of 2QT/2t is determined at 80, and the appropriate QT_Bin is determined at 81. The same steps are carried out mutatis mutandis, at 82, 83 and 84. It is to be noted that other properties, e.g., T-wave amplitude, can be processed in the same manner.

Figure 5A:
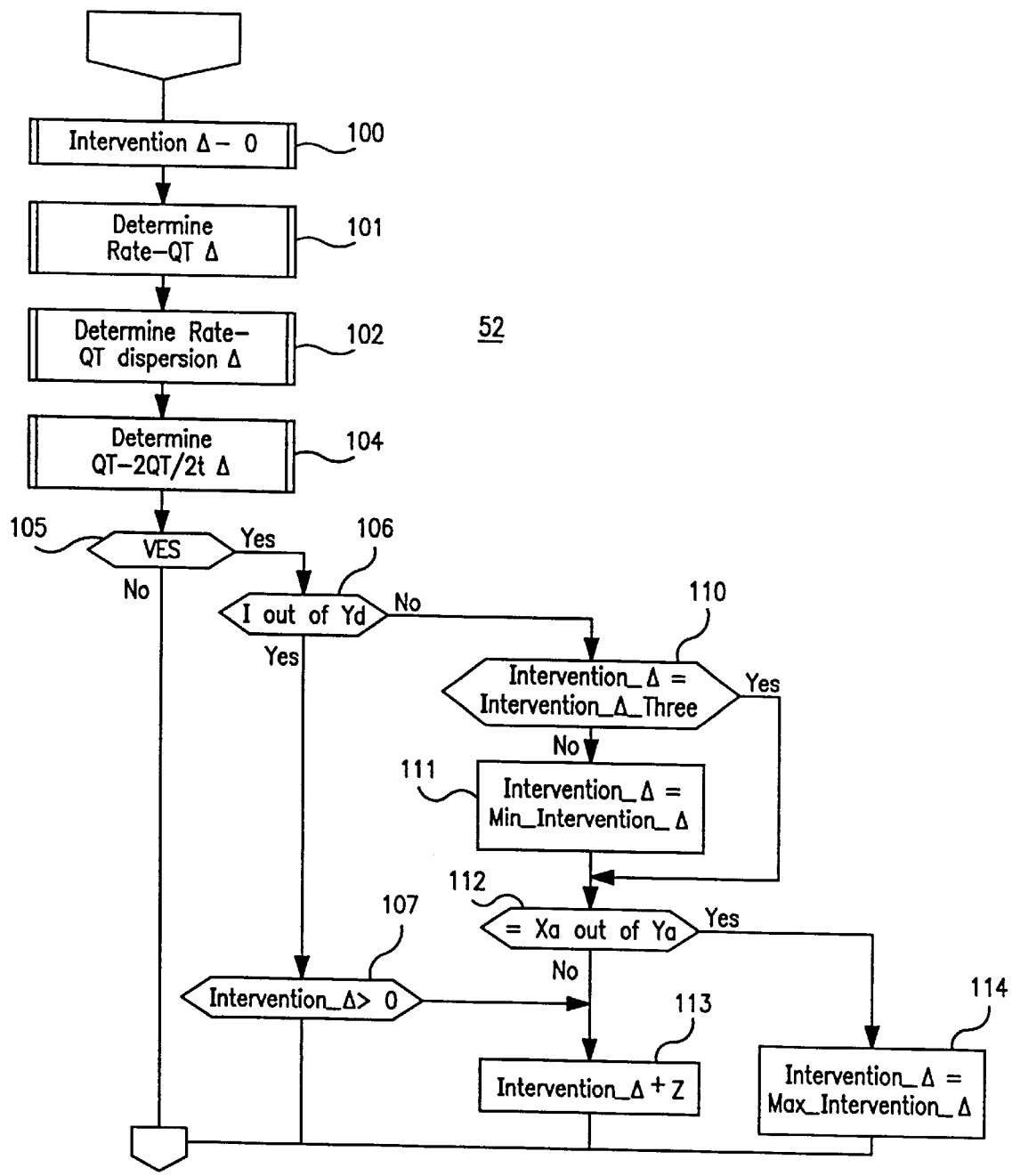
FIG. 5A is a flow diagram illustrating the primary steps taken by the pacemaker in accordance with this invention in providing ventricular arrhythmia prevention pacing therapy.
Figure 5D:
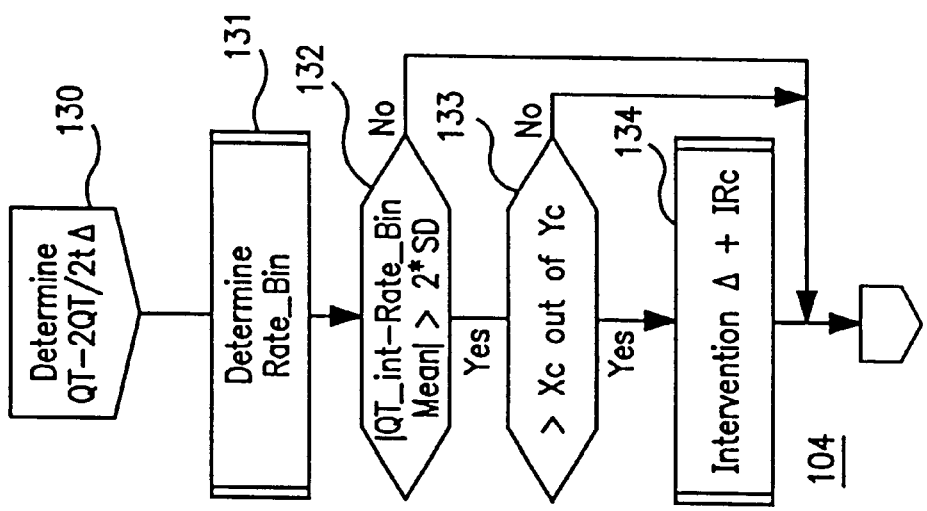
FIG. 5D is a flow diagram illustrating the primary steps taken in analyzing QT dynamics data and in determining the weight to be given to such QT dynamics data in adjusting the intervention pacing rate.
Figure 5C:
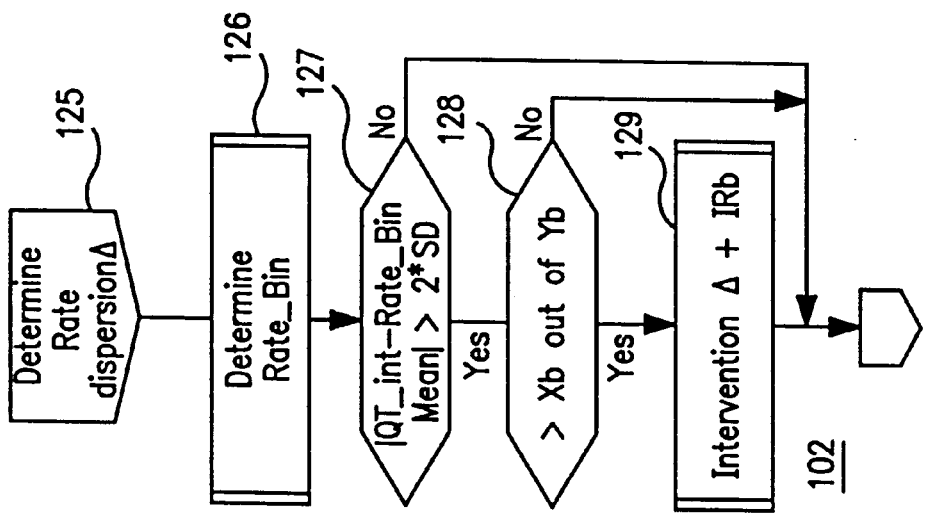
FIG. 5C is a flow diagram representing the steps taken in analyzing QT dispersion data and determining the weight given to such dispersion data in adjusting intervention pacing rate.
Figure 5B:
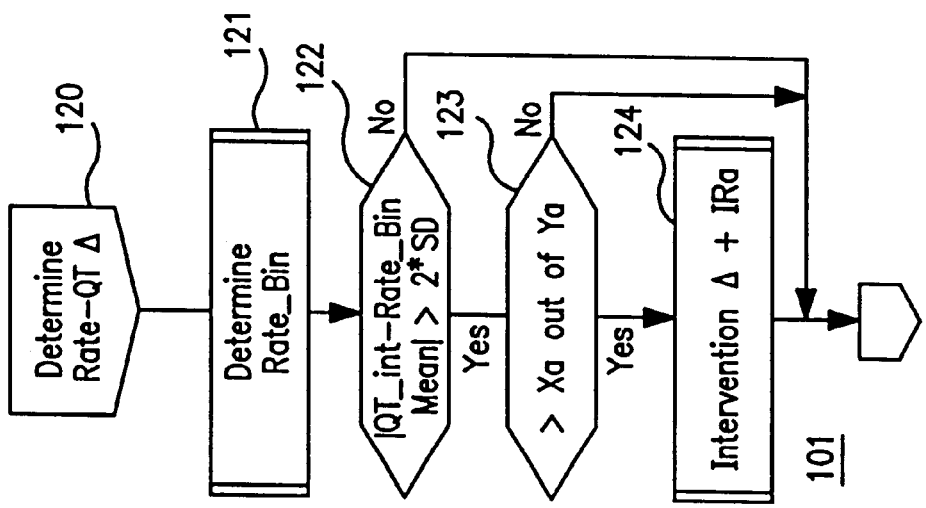
FIG. 5B is a flow diagram representing the primary steps taken in analyzing QT interval data and determining the influence of such QT data on intervention pacing rate.

Referring now to FIG. 5A, there is shown a detailed flow diagram for determining preventive pacing therapy. At 100, the variable "intervention_Δ" is set equal to 0. This variable is computed each cycle, following updating of the data in the Learning Phase to provide a basis for determining whether intervention pacing is to be carried out. Next, at blocks 101, 102 and 104, incremental Rate-QTΔ; QT-dispersionΔ; and 2QT/2t) are determined, as shown in FIGS. 5B, 5C and 5D respectively. In FIG. 5B, Rate-QT) is entered at 120. At 121, the current rate bin is determined, and at 122 the absolute value of QT_int - Rate_Bin_Mean is compared to 2*SD. If the difference value is not greater than 2*SD, the routine exits. If it is greater, it goes to 123 where the pacemaker determines whether QT_int has been greater than QT_int_ Mean by more than 2*SD during $X_a$ cycles out of the last $Y_a$ cycles. If yes, then at 124 intervention_Δ is incremented by a predetermined value $IR_a$. If the answer at 123 is no, the Intervention_Δ is not increased, meaning that the QT_int as a property does not yet contribute to a possible intervention.

Referring to FIG. 5C, the same steps mutatis mutandis are taken at blocks 125, 126, 127, 128 and 129, resulting in possible further increase in intervention_Δ by the predetermined value $IR_b$, if the conditions at 127 and 128 are met. Thus, if the change in dispersion corresponding to the applicable rate bin has been sufficient to meet the criteria, then the value of Intervention_Δ is increased by the value of $IR_b$.

Referring now to FIG. 5D, the same steps are taken mutatis mutandis for the property 2QT/2t at blocks 130–134.

Thus, if the difference between MQT/Mt and the prior mean value of the appropriate QT bin is greater than 2*SD (at 132) and this has been the case for $X_c$ out of $Y_c$ prior cycles (at 133), then Intervention_Δ is incremented by the predetermined value $IR_c$. It is noted that the values $IR_a$, $IR_b$, and $IR_c$ can be programmed in accordance with observed characteristics of the patient, so as to give each optimum weighting.

Referring back to FIG. 5A, following determination of the changes to Intervention_Δ, at 105 it is determined whether there has been a VES. If no, the routine exits with Intervention_) unchanged. However, if there has been a VES, at 106 it is determined whether this is the only VES out of the last $Y_d$ cycles. If yes, the routine goes to 107 and it determines whether Intervention_Δ is already greater than 0. If yes, the routine goes to 113 and doubles the value of Intervention_Δ, to reflect the significance of a VES occurrence. If the answer at 106 is no, indicating that there have been other VES events during the last $Y_d$ cycles, the routine goes to 110 and determines whether Intervention_Δ is greater than a predetermined threshold. If no, then at 111 Intervention_) is set to a minimum value; if yes, the routine skips to 112 and determines whether there have been VES events in more than a predetermined number $X_e$ out of the last $Y_e$ cycles. If no, the routine goes to 113 and doubles the value of Intervention_Δ. However, if yes, the routine goes to 114 and sets Intervention_Δ to a maximum value.

Figure 6:
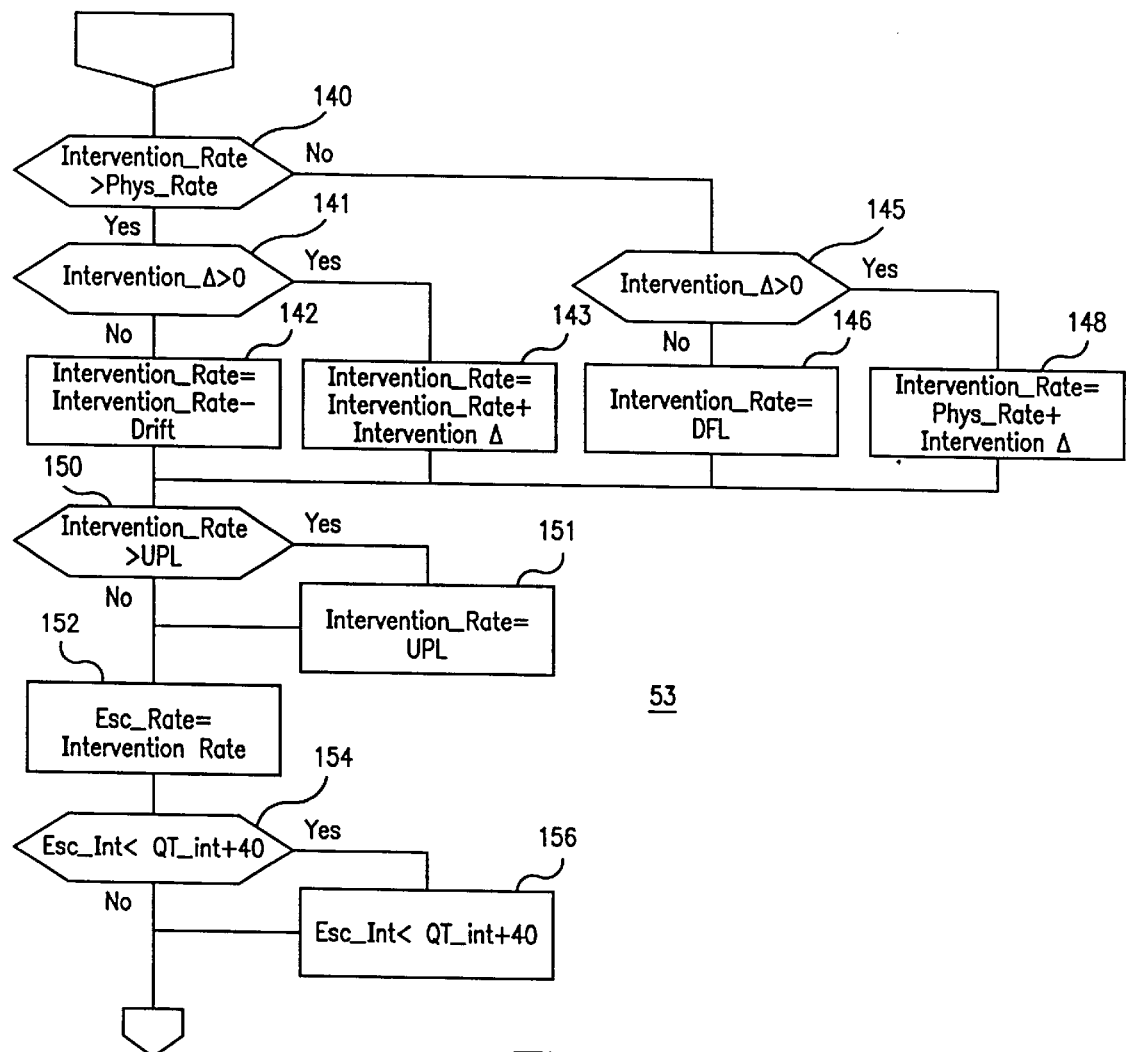
FIG. 6 is a flow diagram illustrating the primary steps taken in determining limits placed on the intervention rate for treating TdP or other ventricular arrhythmias in accordance with this invention.

Referring now to FIG. 6, there is shown a routine for determining rate limits for the intervention rate. At 140, it is determined whether the current intervention rate is greater than the phys_rate. If yes, the routine goes to block 141 and determines whether the Intervention_Δ is greater than 0. If no, suggesting an absence of an indication of indication of TdP, at 142 intervention rate is decremented by predetermined drift factor. However, if yes at 141, the routine goes to 143 and increments intervention rate by the determined value of Intervention_Δ. Going back to block 140, if intervention rate is equal to or less than phys_rate, the routine branches to 145 and determines whether Intervention_Δ is greater than 0. If no, intervention rate is set at the current pacing rate, or dynamic pacing rate (DPL). However, if Intervention_Δ is greater than 0, the routine goes to 148 and sets the intervention rate to phys_rate+Intervention_Δ. Thus, the intervention rate is adjusted depending upon where it currently is with respect to the patient's physiological rate, and depending upon the QT signal analysis carried out in TdP pacing therapy routine.

Still referring to FIG. 6, at 150 it is determined whether the calculated Intervention_Rate is greater than the upper pacing limit (UPL). If yes, it is limited to UPL at 151. At 152, the escape rate is set to correspond to the Intervention_Rate. At 154, it is determined whether the escape interval is less than QT_int+40. The reason for this is that if a large rate jump is required, QT interval may still be so large that the intervention pace pulse may be delivered during the T wave. For this reason, the Esc_int is limited to the value of QT_int plus a predetermined value, e.g., 40 ms. It is to be noted that when the QT interval shortens because of the Intervention_Rate increase, then the escape rate can be increased further accordingly.

There is thus disclosed a pacemaker system and method for systematically analyzing signal data so as to determine if there has been a VES, and if the QT signal has properties indicative of changing conditions which suggest TdP or another dangerous ventricular arrhythmia. The preferred embodiment has been illustrated wherein three such QT properties are utilized, along with VES. However, it is within the scope of this invention to incorporate n routines for analysis of n properties of the QT signal, and a determination of an intervention rate based upon appropriate weighting of each of the n properties. As noted, T-wave amplitude data can be processed and used in the determination. It is to be noticed further that in the illustrated preferred embodiment, the occurrence of a VES event is utilized to increment the intervention rate; and the frequency of recent VES events is used in determining the amount of change in intervention rate.

Figure 7:
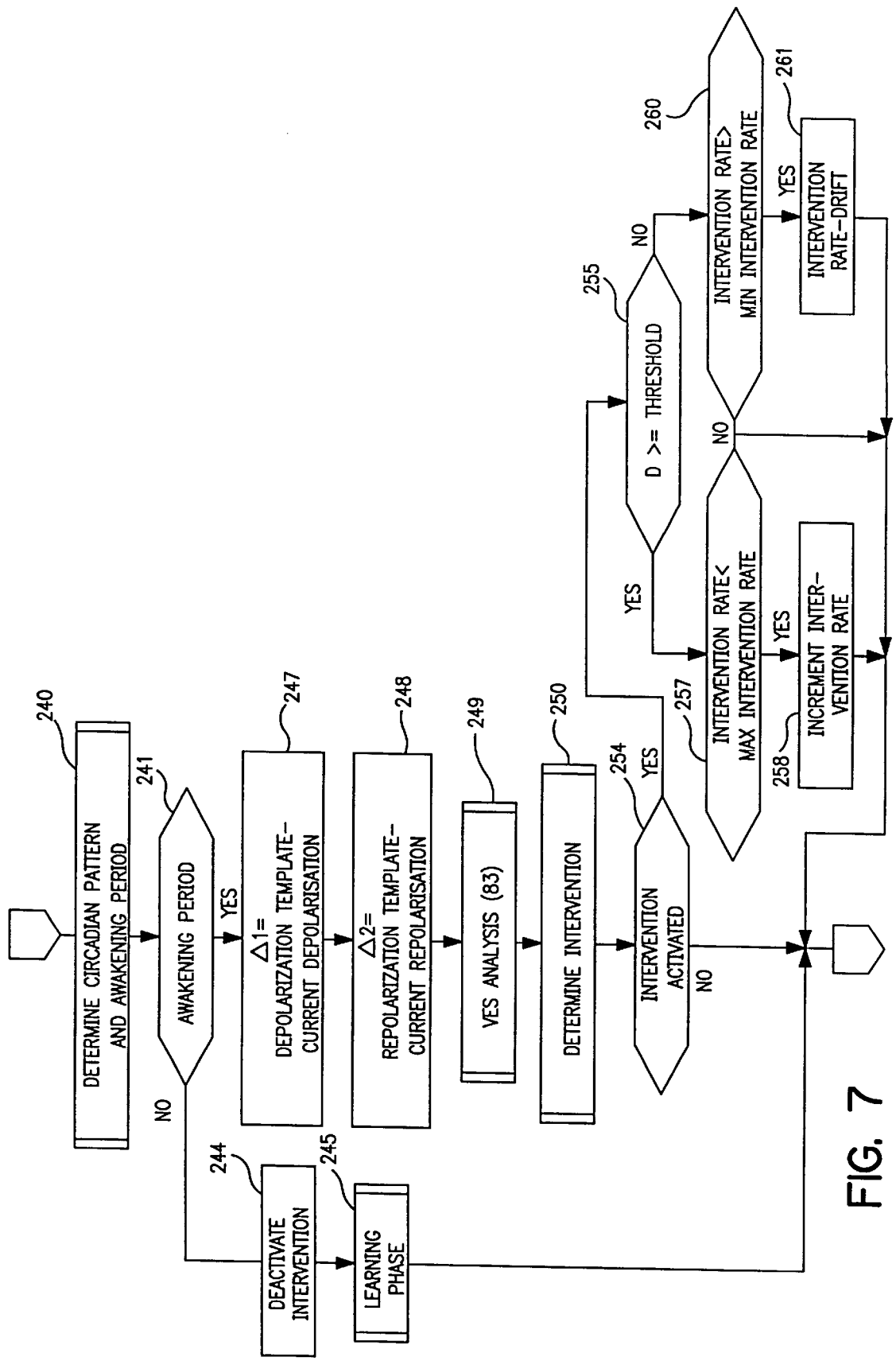
FIG. 7 is an overview flow diagram illustrating the cyclical operations of another VT Prevention routine in accordance with this invention.

Referring now to FIG. 7, there is shown a flow diagram of steps taken in accordance with a VT prevention feature of this invention. The VT prevention feature is directed to detecting conditions during patient awakening that suggest the onset of VT. This feature can be incorporated instead of the Long QT syndrome feature, or in addition. At 240, a routine is run for determining the patient awakening period. Any criteria can be used for determining "awakening"; reference is made to U.S. Pat. No. 5,861,011, and incorporated herein by reference. At 241 the pacemaker determines whether the patient is in fact in the awakening period. If no, at 244 the intervention state is deactivated, and at 245 the pacemaker goes into the learning phase, the details of which are set forth in the connection with FIG. 8.

If the patient is in the awakening period, the pacemaker goes on to process current information concerning the depolarization (QRS) and repolarization (T wave) waveforms. At 247, the pacemaker obtains the depolarization template for the current cycle, and compares it to the depolarization template which was generated during the learning phase. The difference is computed and stored as Δ1. Likewise, at step 248, the pacemaker gets the current repolarization template and compares it with the stored repolarization template from the learning phase, and generates a Δ2, which is representative of the difference. Then, at block 249, the pacemaker goes through a VES analysis, to obtain a measure ( )Δ3) of whether there has been a ventricular extra systole, and how close the coupling interval was to the patient's mean QT interval. The VES analysis is set forth in particular detail in FIG. 9. Following this, the pacemaker goes to block 250, and determines whether intervention is indicated, based upon data gathered and generated at blocks 247, 248, and 249 above. The Determine Intervention routine is set forth in detail at FIG. 10.

Still referring to FIG. 7, at block 254, the pacemaker determines whether intervention has been activated. If no, the routine exits, and the pacemaker continues to set the pacing escape intervals in a normal way. However, if yes, the routine branches to block 255, and determines whether the variable D is equal to or greater than a predetermined threshold. D is calculated in the Determine Intervention routine 250, and represents a summation of the respective Δ values calculated at blocks 247, 248, which are representative of refractoriness dispersion; and also the Δ value calculated at 249, which represents the presence of a dangerous VES. The calculation of D is discussed in more detail in connection with FIG. 10. If D is equal to or greater than threshold, at 257 the pacemaker determines whether the intervention rate remains less than the maximum intervention rate. If yes, intervention rate is incremented at 258; if no, intervention rate is at its maximum allowable value and the routine exits. If, at 255, D is not up to threshold, then at 260 it is determined whether the intervention rate is higher than the minimum intervention rate. If yes, at 261 intervention rate is decremented by subtracting a programmable drift value; if no, the intervention rate is as low as is allowed, and the routine exits.

Figure 8:
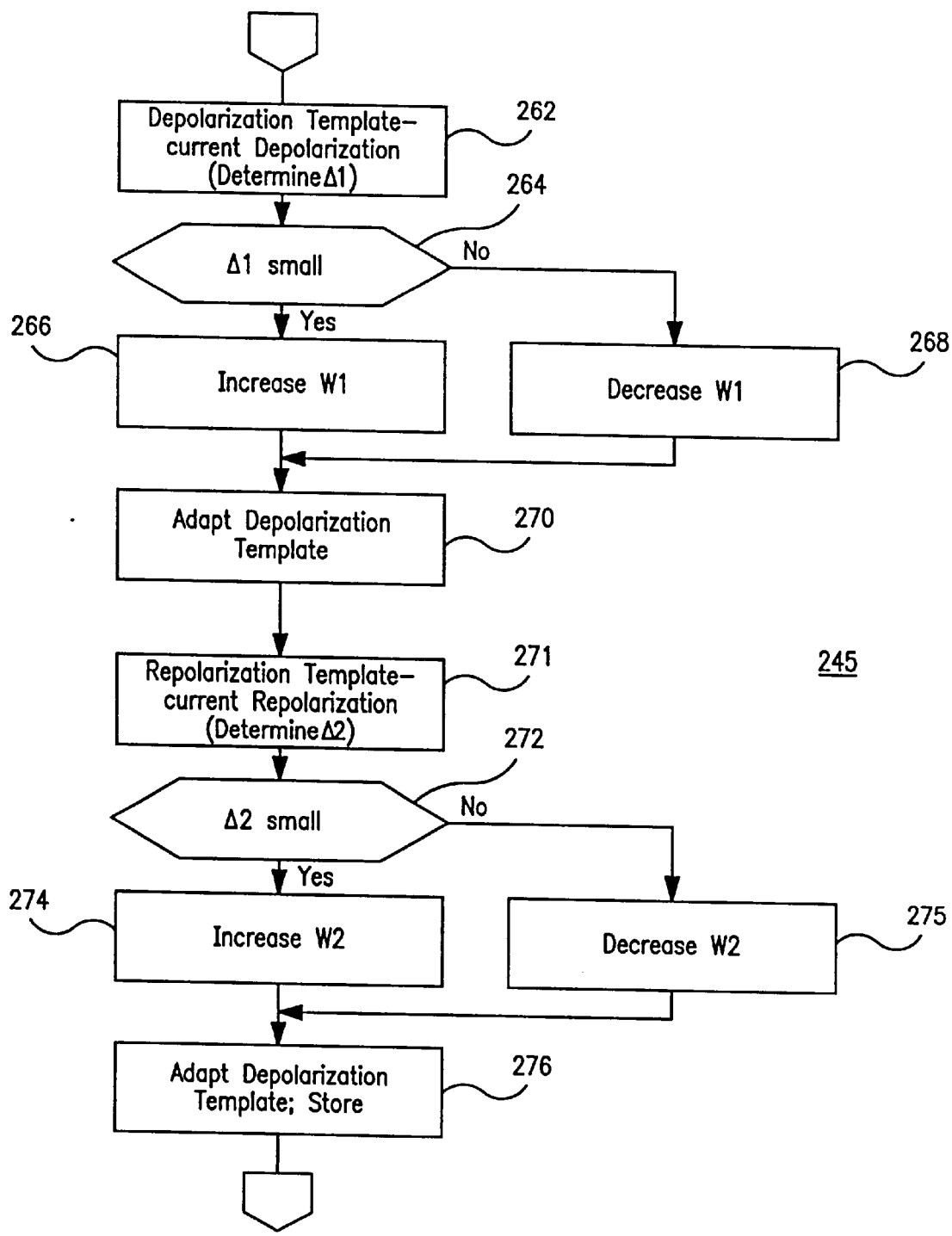
FIG. 8 is a simplified flow diagram illustrating the primary steps taken in carrying out the Learning Phase portion of the VT Prevention routine of FIG. 7.

Referring now to FIG. 8, there is shown a flow diagram of the learning phase routine 245, in accordance with this invention. As discussed in connection with FIG. 7, this phase is entered when the patient is not in the awakening period. At 262, the pacemaker calculates a variables Δ1 which constitutes the depolarization template then stored in memory, minus the current depolarization template for the just detected R wave. In obtaining a template, the wave signal data is placed into digital form by an A–D converter, which is part of the function provided by signal processor block 27. Obtaining waveform templates is well known in the art, and any suitable hardware or software arrangement can be used in this invention. In a preferred embodiment, digital samples are obtained representing the waveform amplitude along successive time increments, from the beginning of the wave to the end, and are stored. In determining the Δ difference, the respective waveform amplitude values are subtracted, and the difference is integrated over the time domain. In a preferred embodiment, the template generation and template difference calculations are performed by dedicated hardware, as shown at 27. However, any combination of hardware and software can be utilized.

Next, at 264, it is determined whether the )1 value is small. The reason for making this determination is that large variations during the learning phase suggest that the signal is not stable enough to be a reference during the awakening period. Consequently, if the deviation found at 264 is statistically small (indicating stability), at 266 a weighting factor W1 is increased; if the deviation is not statistically small, then at 268 the W1 is decreased. These weighting factors are utilized in the subsequent determination of intervention in routine 250. Next, at block 270, the depolarization template is adapted so as to be changed toward the most recently detected depolarization template. This can be done, e.g., by matching the minimum values and slopes of the depolarization template and the new QRS wave, and adjusting each sample of the template incrementally toward the samples of the new QRS. The functions are suitably carried out by the microprocessor of block 20.

Still referring to FIG. 8, blocks 271, 272 and 274–276 represent corresponding steps for the repolarization template, which reflects the sensed T wave. At 271, the deviation Δ2 is determined, by subtracting the just obtained repolarization wave from the stored repolarization template. At 272, it is determined whether the deviation is small, representing a stable signal. If yes, weighting factor W2 is increased at 274; if no, W2 is decreased at 275. The repolarization template is then adapted and stored at 276.

Referring now to FIG. 9, there is shown a flow diagram of the routine 249 for carrying out VES analysis. This is done because VT is often initiated or preceded by one or more ventricular extra-systoles if the patient heart rate is low enough and the coupling interval is critical, i.e., VES occurs near or in the vulnerable phase. In this situation likewise, intervention may be indicated, so the pacemaker of this invention collects VES data which is included in the Determine Intervention routine.

At block 282, it is determined whether there has been a VES. If no, the routine branches to block 283, and sets Δ3 (the deviation value corresponding to VES analysis) to zero. However, if there has been a VES, then it has to be determined how critical the VES is deemed. At 285, the pacemaker compares the coupling interval (the interval from the prior R wave to the ΔVES to the current QT interval. If the coupling interval minus the current QT interval is less than or equal to a stored critical phase value, then the VES is deemed very critical, and at 290 Δ3 is given a weighted VERY_CRITICAL value. However, if the answer at 285 is no, then the routine goes to 286 and determines whether there have been a predetermined number n VES occurrences in the last m intervals, where n and m are programmable numbers. If yes, the VES occurrence is deemed critical, and at block 287 Δ3 is given a weighted CRITICAL value which is somewhat less than the VERY_CRITICAL value. If the answer at 286 is no, at 288 Δ3 is given a LOW_CRITICAL weighting. At routine 249, the values assigned to Δ3 include the weighting factor, such that the stored deviation is assumed to be accompanied by a weighting factor of 1 for the calculation which is carried out at block 277.

Referring now to FIG. 10, there is shown a flow diagram of the Determined Intervention routine 250. At step 277, the pacemaker determines the total deviation D, which is calculated by taking the sum of all the separate deviations, each multiplied by its respective weighting factor W. In the preferred embodiment as illustrated, there are three different deviations determined, so the summation is from i=1 to i=3. Thus, each cycle the summation constitutes Δ1 multiplied by the current value of W1; Δ2 multiplied by the current value of W2, and the determined value of Δ3, where the weighting factor is 1 since the value of Δ3 has already been calculated to reflect appropriate weighting. At 278, it is determined whether the current value D is greater than or equal to threshold. If no, intervention is not indicated and the routine exits. However, if D is greater than or equal to the programmed threshold, then intervention is activated at step 280, suitably by setting a flag to store the fact that intervention has been activated. As seen in FIG. 7, once intervention has been activated, it is not deactivated until the awakening period is over, at which time the pacemaker proceeds to block 244 and deactivates intervention. As per the above discussion of FIG. 7, if D drops below threshold when Intervention is activated, the Intervention rate is decremented toward a lower limit.

Recapitulating with respect to the VT prevention routine which is carried out during awakening, and referring to FIG. 7, it is seen that during normal periods outside of the awakening period, both daytime and nighttime, the pacemaker is continually adapting the depolarization and repolarization templates in the learning phase. When the patient is in the awakening period, data represented by deviation values Δ1, Δ2 and Δ3 are obtained at blocks 247, 248 and 249 respectively. Whenever, during the awakening period, the cumulative sum of the deviations exceeds a predetermined threshold, intervention is activated, and the intervention mode is maintained throughout the awakening period. Of course, if the deviation values, which represent refractory dispersion, become small, then the intervention rate drifts down to a lower rate limit, such that there effectively is no overdrive intervention. However, as long as the wave variability remains high, the intervention rate will be maintained so as to provide overdrive pacing calculated to prevent ventricular tachycardia.

It is noted that while three separate deviation measurements are illustrated in the preferred embodiments, additional data can be collected, and weighted accordingly. Additionally, each weighting factor can be programmed to vary within predetermined limits, so that weighting can be adapted in terms of known patient history.

There have been disclosed several embodiments for prevention of ventricular arrhythmias, in particular, by detecting long QT syndrome and by determining when the patient is vulnerable to VT during awakening. The embodiments of this invention use VES data, QT data, or VES and QT data for determining the onset of a dangerous arrhythmia, and for determining overdrive pacing rate.

What is claimed is:

1. a pacemaker system for pacing a patient, said pacing including overdriving the patient's heart for prevention of ventricular arrhythmias, said system having ventricular generator means for generating and delivering ventricular pace pulses, and ventricular sense means for sensing QT signals, said system further comprising:

QT analysis means for analyzing at least two properties of the patient's QT signal and for obtaining QT data representative variations of said at least two respective properties of said QT signal, said QT analysis means comprising means for analyzing QT interval and QT dispersion as said at least two properties;

VES means for determining when ventricular extra systoles occur and for generating VES data representative of said occurrences;

intervention means for determining from said QT data and said VES data when intervention is indicated order to treat a ventricular arrhythmia; and rate means for controlling said ventricular generator means to generate and deliver pacing pulses at an intervention rate greater than the patient's natural rate in response to a said indication;

wherein said QT analysis means comprises means for continually determining a means value and standard deviation value of each of said QT properties and for updating said values when a respective QT property exceeds its mean value by more than n times its standard deviation.

2. A pacemaker system or pacing a patient, said pacing including overdriving the patient's heart for prevention of ventricular arrhythmias, said system having ventricular generator means for generating and delivering ventricular pace pulses, and ventricular sense means for sensing QT signals, said system further comprising:

QT analysis means for analyzing at least two properties of the patient's QT signal and for obtaining QT data representative of variations of said at least two respective properties of said Qt signal, said QT analysis means comprising means for analyzing QT interval and QT dispersion as said at least two properties;

VES means for determining when ventricular extra systoles occur and for generating VES data representative of said occurrences;

intervention means for determining from said QT data and said VES data when intervention is indicated in order to treat a ventricular arrhythmia; and rate means for controlling said ventricular generator means to generate and deliver pacing pulses at an intervention rate greater than the patient's natural rate in response to a said indication;

wherein said intervention means comprises a respective variation means for determining respective measures of variation of each of said properties, and composite means for obtaining a composite measure of QT property variations from said respective measures, and wherein a change means comprises means for changing said intervention rate as function of said composite measure.

3. The pacemaker system as described in claim 2, wherein said change means comprises means for changing said intervention rate as a function of said composite measure and said VES data.

4. A pacemaker system for pacing a patient, said pacing including overdriving the patient's heart for prevention of ventricular arrhythmias, said system having ventricular generator means for generating and delivering ventricular pace pulses, and ventricular sense means for sensing QT signals, said system further comprising:

QT analysis means for analyzing at least two properties of the patient's QT signal and for obtaining QT data representative of variations of said at least two respective properties of said QT signal;

VES means for determining when ventricular extra systoles occur and for generating VES data representative of said occurrences;

intervention means for determining from said QT data and said VES data when intervention is indicated in order to treat a ventricular arrhythmia; and rate means for controlling said ventricular generator means to generate and deliver pacing pulses at an intervention rate greater than the patient's natural rate in response to a said indication;

wherein said VES means comprises means for determining the recent frequency of VES occurrences, and said intervention means comprises means for determining change of said intervention rate as a function of frequency of VES occurrences.

5. A pacemaker system for pacing a patient, said pacing including overdriving the patient's heart for prevention of ventricular arrhythmias, said system having ventricular generator means for generating and delivering ventricular pace pulses, and ventricular sense means for sensing QT signals, said system further comprising:

QT analysis means for analyzing at least two properties of the patient's QT signal and for obtaining QT data representative of variations of said at least two respective properties of said QT signal;

VES means for determining when ventricular extra systoles occur and for generating VES data representative of said occurrences;

intervention means for determining from said QT data and said VES data when intervention is indicated in order to treat a ventricular arrhythmia; and rate means for controlling said ventricular generator means to generate and deliver pacing pulses at an intervention rate greater than the patient's natural rate in response to a said indication; and limit means for limiting the increase of said intervention rate to a rate which corresponds to an escape interval which is at least as great as the current QT interval plus a predetermined value.

6. A pacemaker system for pacing a patient's heart, said system having generator means for generating and delivering ventricular pace pulses and sensing means for sensing patient ventricular signals, comprising:

QT means for obtaining and storing data representative of the patient's QT signal;

analyzing means for analyzing said QT data to obtain parameter values representative of a plurality of respective QT parameters, and comparison means to compare each parameter value with a statistical measure of recent said parameter values to obtain a change measure representative of change of each said parameter;

intervention means for determining, as a function of said change measures, an intervention pacing said patient so as to provide therapy for long QT syndrome; and control means for controlling said generator means to generate and deliver ventricular pace pulses at said intervention rate wherein said analyzing means further comprises:
first means for obtaining values representative of QT interval;
second means for obtaining values representative of QT dispersion; and
third means for obtaining values representative of QT time derivative.

7. A pacemaker system for pacing a patient's heart, said system having generator means for generating and delivering ventricular pace pulses and sensing means for sensing patient ventricular signals, comprising:

QT means for obtaining and storing data representative of the patient's QT signal;

analyzing means for analyzing said QT data to obtain parameter values representative of a plurality of respective QT parameters, and comparison means to compare each parameter value with a statistical measure of recent said parameter values to obtain a change measure representative of change of each said parameter;

intervention means for determining, as a function of said change measures, an intervention pacing rate for pacing said patient so as to provide therapy for long QT syndrome; and control means for controlling said generator means to generate and deliver ventricular pace pulses at said intervention rate wherein said analyzing means further comprises T-wave amplitude means for analyzing T-wave amplitude, and means for determining a measure of change in T-wave amplitude.

8. The pacemaker system as described in claim 7, comprising means for obtaining a statistical measure of each said QT parameter.

9. A pacemaker system for pacing a patient's heart, said system having generator means for generating and delivering ventricular pace pulses and sensing means for sensing patient ventricular signals, comprising:

VES means for obtaining and storing VES data representative of VES occurrences;

intervention means for determining, as a function of said VES data, an intervention pacing rate for pacing said patient so as to provide overdrive pacing therapy; and control means for controlling said generator means to generate and deliver ventricular pace pulses at said intervention rate;

wherein said intervention means comprises means for incrementing said intervention pacing rate by a minimum increment when there has been just one VES in the last Y cycles.

10. The pacemaker system as described in claim 9, wherein said intervention means comprises means for incrementing said intervention pacing rate by more than said minimum increment when there has been a VES occurrence during X of the last Y cycles.

11. A pacemaker system for pacing a patient's heart, said system having generator means for generating and delivering ventricular pace pulses and sensing means for sensing patient ventricular signals, comprising:

VES means for obtaining and storing VES data representative of VES occurrences;

intervention means for determining, as a function of said VES data, an intervention pacing rate for pacing said patient so as to provide overdrive pacing therapy;

control means for controlling said generator means to generate and deliver ventricular pace pulses at said intervention rate; and VES frequency means for determining a measure of the frequency of said VES occurrences, and wherein said invention means comprises means for determining said intervention pacing rate as a function of said VES frequency measure.

* * * * *